(12) United States Patent
Lutz

(10) Patent No.: US 8,236,554 B2
(45) Date of Patent: Aug. 7, 2012

(54) BIOGAS PLANT FOR METHANIZING BIOMASS HAVING A HIGH SOLIDS FRACTION

(75) Inventor: Peter Lutz, Munich (DE)

(73) Assignee: Bekon Energy Technologies GmbH & Co., KG, Unterfohring (DE)

(*) Notice: Subject to any disclaimer, the term of this patent is extended or adjusted under 35 U.S.C. 154(b) by 37 days.

(21) Appl. No.: 12/645,330

(22) Filed: Dec. 22, 2009

(65) Prior Publication Data

US 2010/0159571 A1 Jun. 24, 2010

(30) Foreign Application Priority Data

Dec. 23, 2008 (DE) ............... 20 2008 017 049 U
Mar. 5, 2009 (DE) ............... 10 2009 011 868

(51) Int. Cl.
C12M 1/36 (2006.01)
C12M 1/00 (2006.01)
B01D 21/24 (2006.01)

(52) U.S. Cl. ........... 435/286.5; 435/286.6; 435/289.1; 435/290.1; 210/104; 210/767

(58) Field of Classification Search ........... 435/286.5, 435/286.6, 289.1, 290.1; 210/104, 767
See application file for complete search history.

(56) References Cited

U.S. PATENT DOCUMENTS

| | | | | |
|---|---|---|---|---|
| 4,568,457 A | * | 2/1986 | Sullivan | ............ 210/151 |
| 5,786,209 A | * | 7/1998 | Newberg | ............ 435/309.2 |
| 7,445,927 B2 | * | 11/2008 | Maga et al. | ............ 435/289.1 |
| 2004/0172878 A1 | | 9/2004 | Krylowicz et al. | |
| 2009/0068725 A1 | | 3/2009 | Lutz | |

FOREIGN PATENT DOCUMENTS

| | | |
|---|---|---|
| DE | 44 09 487 A1 | 4/1995 |
| DE | 195 32 359 A1 | 3/1997 |
| DE | 20 2005 013 389 U1 | 1/2006 |
| DE | 10 2006 009 652 A1 | 8/2007 |
| RU | 2297395 C2 | 4/2007 |
| WO | WO-02/06439 A2 | 1/2002 |
| WO | WO-02/06439 A3 | 1/2002 |
| WO | WO-2007/096392 A1 | 8/2007 |

OTHER PUBLICATIONS

Eurasion Search Report mailed Apr. 29, 2010, for EA Application No. 200901570, one page.

* cited by examiner

*Primary Examiner* — Nathan Bowers
*Assistant Examiner* — Gautam Prakash
(74) *Attorney, Agent, or Firm* — Morrison & Foerster LLP

(57) ABSTRACT

A biogas plant for methanizing biomass having a high solids fraction includes a digestion tank system having a plurality of digestion tanks adapted to be closed in a gas- and liquid-tight manner, each of which includes a charging and withdrawing opening for charging with biomass and withdrawing the biomass, a biogas discharge means, a percolate reservoir, a percolate drainage means for discharging percolate from the plurality of digestion tanks and supplying the percolate to the percolate reservoir, a percolate distributing means for distributing the percolate from the percolate reservoir over the biomass in the plurality of digestion tanks, and a percolate regulating means for regulating the percolate level in the plurality of digestion tanks. The percolate reservoir includes a first and a second percolate container, and supplying and discharging of percolate to/from the first and/or the second percolate container takes place with the aid of the percolate regulating means.

17 Claims, 2 Drawing Sheets

BIOGAS PLANT FOR METHANIZING BIOMASS HAVING A HIGH SOLIDS FRACTION

CROSS-REFERENCE TO RELATED APPLICATIONS

The present application is based on, and claims priority to German Patent Application No. 202008017049.4, filed Dec. 23, 2008 and German Patent Application No. 102009011868.3, filed Mar. 5, 2009 the disclosures of which are incorporated herewith in their entirety.

FIELD

The present invention relates to a biogas plant for methanizing biomass, in particular biomass having a high solids fraction, in accordance with the preamble of claim 1.

BACKGROUND

The expression "biomass having a high solids fraction" is to be understood as meaning the opposite of liquid, pumpable biomass, such as is used in wet fermentation processes. "Biomass having a high solids fraction" should therefore be understood as non-pumpable biomass.

A biogas plant in accordance with the preamble of claim 1 is known from WO 2007/096392. This known biogas plant includes a plurality of digestion tanks which are adapted to be closed in a gas- and liquid-tight manner, each of which includes a percolate discharge conduit having a percolate pump and opening into a common percolate reservoir. Percolate may be conveyed back from the common percolate reservoir into the digestion tank via a percolate return line in which a percolate recirculation pump is provided and which branches toward the individual digestion tanks. The filling level or percolate level of the individual digestion tanks is detected by respective filling level sensors having the form of pressure sensors.

This known biogas plant has the drawback that the plurality of digestion tanks has to be considered as a homogeneous overall system, for each digestion tank receives the same percolate, with substantially identical conversion processes taking place in every digestion tank in this overall system. This known biogas plant is therefore homogeneous in terms of process technology and is cumulatively composed of a plurality of partial systems (the individual digestion tanks) as regards its capacity.

SUMMARY

Starting out from the biogas plant according to WO 2007/096392, it is an object of the present invention to specify a biogas plant having a plurality of digestion tanks which is more flexible with a view to the conversion processes in the individual digestion tanks while forming a heterogeneous overall system in terms of process technology.

This object is achieved through the features of claim 1.

In accordance with the present invention, the percolate reservoir includes a first and a second percolate container that are each adapted to be connected via a system of conduits to each single one of the plurality of digestion tanks, wherein feeding and discharging of the percolate to and from the percolate containers may be regulated separately for each digestion tank. Accordingly, there exist two separate percolate circuits, so that a first subset of the digestion tanks may receive percolate from the first percolate container, and a second subset of the digestion tanks may receive percolate from the second percolate container. Analogously, the percolate is conveyed from the first subset of the digestion tanks back into the first percolate reservoir, and the percolate from the second subset of the digestion tanks is conveyed back into the second percolate container. In this way it is possible, for instance, for Nawro's (nachwachsende Rohstoffe=renewable resources) to be converted to biogas in the first subset of digestion tanks, whereas the organic fraction of domestic waste is converted in the second subset of the digestion tanks. If both types of biomass were to receive the same percolate, the percolate from the contaminated organic fraction of the domestic waste would "pollute" the "purer" percolate of the renewable resources. The production of biogas would not unfold optimally in either type of digestion tank, for neither the renewable resources nor the organic fraction of the domestic waste receives the percolate that is particularly suited for each one of them. As a result of the percolate circuits being separated from each other, the percolate may be adapted to the respective biomass to be fermented—e.g., renewable resources or separately collected organic waste and organic domestic waste fraction. As it were, in terms of process technology one biogas plant thus becomes two biogas plants which jointly produce biogas.

In accordance with claim 12 it is also possible to provide more than two separate percolate circuits. The number of separate percolate circuits having associated percolate containers determines the number of different biomasses that can be fermented in the biogas plant of the invention.

In accordance with the features of claim 2, a first and a second main drainage line coming from the first and second percolate containers branch into respective digestion tank drainage lines, so that every digestion tank may be connected to the first and/or the second percolate container. In operation, a separation of the first and second conversion processes is realized, to the effect of any digestion tanks in which the first conversion process takes place being connected to the first percolate container, and any digestion tanks in which the second conversion process takes place being connected to the second percolate container. What process takes place in which digestion tank may be determined at will in accordance with the invention.

In accordance with an aspect according to claim 3, the percolate is filtered prior to its introduction into the percolate reservoir. Such filtering may also be provided, alternatively or additionally, in the lines recirculating the percolate from the percolate reservoir to the digestion tanks. Filtering ensures that the distribution unit, e.g. a spraying unit, will not be clogged by the dirt particles, suspended matter, etc. that are present in the percolate. Furthermore it is possible to remove heavy metals and the like from the percolate by such filtering.

As a result of the features of claim 4 a constructive simplification is achieved, to the effect that—instead of a separate line leading from each one of the two main drainage lines into each one of the digestion tanks—a single line referred to as a main drainage section leads out from each one of the digestion tanks, which single lines then branch into respective lines that are referred to as a first and a second secondary drainage section and that are connected to the first and the second main drainage line, respectively. By controlling cut-off valves arranged in the secondary drainage sections it is possible to connect each one of the digestion tanks to the first and/or the second percolate container.

The features of claim 5 allow an arbitrary three-dimensional relationship between the digestion tanks and the percolate reservoir. In particular, the percolate reservoir may be disposed in a higher position than the digestion tanks, for the percolate may be transported to this higher position with the aid of the pumps.

As a result of the features of claim 6, the digestion tanks may be charged and emptied independently of each other, for the percolate level of each individual digestion tank is detected. The data (height of the percolate level) detected by the percolate regulation unit with the aid of the filling level sensor are supplied, in accordance with the conditions in the digestion tanks, as an appropriate signal to the respective pumps which lower the percolate level to target level by pumping off percolate. The target level may be determined, e.g., on the basis of the charged quantity of the digestion tank or the composition of the biomass, or the like.

In the bioreactor of the invention, the percolate drainage means and the percolate distributing means for withdrawing the percolate from the percolate reservoir and distributing it over the biomass in the digestion tanks have a nearly symmetric construction—Claims 7 and 8.

As a result of the advantageous aspect of the invention according to claim 9 having a plurality of main distributing sections which extend into each one of the digestion tanks while being distributed across the area of cross-section of the digestion tank, a uniform distribution of the percolate over the entire surface of the biomass in a respective digestion tank is facilitated. The uniform distribution of the percolate may furthermore be optimized by a rebounding plate being arranged in a suitable position for each main distributing section, independently of the number of the main distributing sections, on which rebounding plate the percolate exiting from this main distributing section impacts and, rebounding from the latter, is sprayed over the biomass.

Due to a corresponding valve assembly as defined in claims 8 and 11, each one of the digestion tanks may be connected to the first and/or the second percolate container in analogy with the percolate drainage means. Advantageously, control of the valves takes place automatically, such that a respective digestion tank is not connected to different percolate containers via its drainage means and its percolate distributing means.

As a result of the arrangement of the percolate containers in accordance with claim 13, the space demand for the percolate reservoir is reduced in comparison with a side-by-side arrangement of the percolate containers, for instance to about half in a special arrangement in accordance with claim 14. This, moreover, involves a simplified system of conduits connecting the percolate containers to the digestion tanks. In addition, the outer percolate container acts as a thermal insulation jacket for the inner percolate container.

The features of claim 15 allow simple and thus safe charging of the digestion tanks with the aid of appropriate agricultural machines.

In accordance with claim 17, the valves are adapted to be operated pneumatically, so that explosions of the gases developing during the conversion processes, which might be triggered by sparking of electrically operated valves, are excluded.

The remaining subclaims relate to further advantageous aspects of the invention.

BRIEF DESCRIPTION OF THE DRAWINGS

Further features and advantages of the present invention are evident from the following detailed description of a preferred embodiment by making reference to the annexed drawings, wherein.

DETAILED DESCRIPTION

Figure 1:
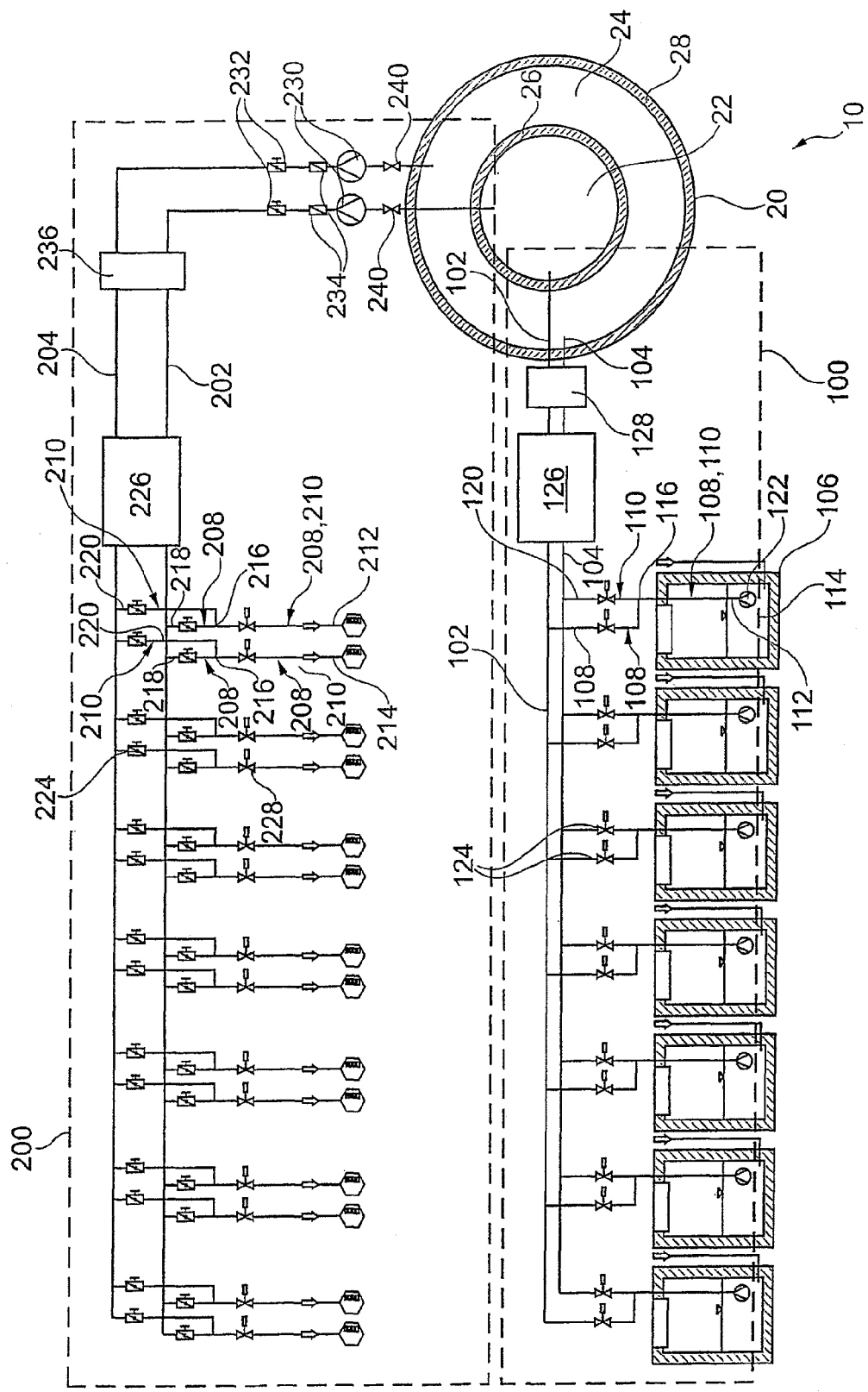
FIG. 1 is a schematic representation of the bioreactor in accordance with a preferred embodiment of the present invention.

In accordance with the schematic representation in FIG. 1, a biogas plant 10 in accordance with a preferred embodiment includes a percolate reservoir 20, a percolate drainage means 100, a percolate distributing means 200, and a plurality (in this embodiment: seven) of digestion tanks 106.

The percolate reservoir 20 includes a first—inner—column-type percolate container 22 and a second—outer—column-type percolate container 24, wherein a partition wall 26 separating the percolate containers 22, 24 from each other and an outer wall 28 of the percolate reservoir 20 form concentric circles in a sectional view.

Figure 2:
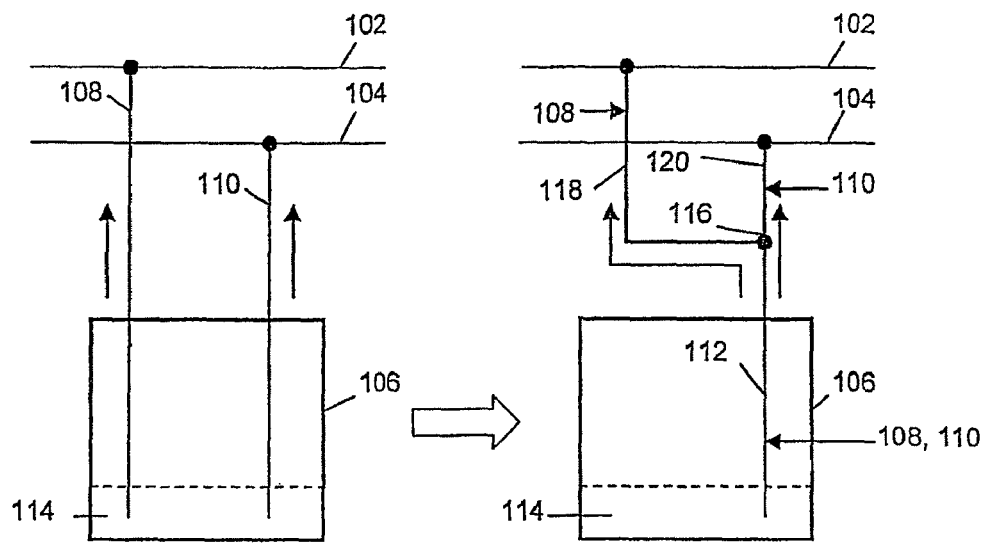
FIG. 2 is a schematic representation of a circuit detail of the percolate drainage means.

The percolate drainage means 100 includes a first main drainage line 102 and a second main drainage line 104 which open into the inner 22 and the outer percolate container 24, and a first and a second digestion tank drainage line 108 and 110, wherein each one of the plurality of digestion tanks 106 is connected to the first main drainage line 102 via a first digestion tank drainage line 108 and to the second main drainage line 104 via a second digestion tank drainage line 110. The first and the second digestion tank drainage line 108 and 110 of a respective digestion tank 106 include a common main drainage section 112 extending from a percolate region 114 inside the digestion tank 106 as far as a branching point 116 outside of the digestion tank 106, and a first and a second secondary drainage section 118 and 120 extending from the branching point 116 to the first and the second main drainage line 102 and 104, respectively. In other words, the first digestion tank drainage line 108 includes the main drainage section 112 and the first secondary drainage section 118, and the second digestion tank drainage line 110 includes the main drainage section 112 and the second secondary drainage section 120, as is shown more clearly (without valves) in FIG. 2.

At each one of the main drainage sections 112 a pump 122 for conveying percolate into the percolate reservoir 20 is arranged, and inside each secondary drainage section 118, 120 there is a cut-off valve 124 whereby the flow through this section may be blocked or enabled. In particular, the percolate conveyed by the pump 122 may be supplied to the second percolate container 24 via the main drainage section 112, the second secondary drainage section 120, and the second main drainage line 104 by closing the cut-off valve 124 in the first secondary drainage section 118 and opening the cut-off valve 124 in the second secondary drainage section 120, and may be supplied to the first percolate container 22 via the main drainage section 112, the first secondary drainage section 118, and the first main drainage line 102 by opening the cut-off valve 124 in the first secondary drainage section 118 and closing the cut-off valve 124 in the second secondary drainage section 120.

As a result of corresponding switching positions of the cut-off valves 124 associated to the digestion tanks 106 it is moreover possible to supply the percolate of the $i^{th}$ digestion tank 106 to the first percolate container 22, and the percolate of the $j^{th}$ digestion tank 106 to the second percolate container 24, wherein $i, j \in \{1, \ldots, n\}$, with n=7 in this embodiment, and i=j (for the case of identical conversion processes in all of the digestion tanks 106, i.e., if a separation is not necessary or desired), or i≠j (in cases of different conversion processes). Between the digestion tanks 106 and the percolate reservoir 20, a first filter system 126 is arranged in the first and second main drainage lines 102 and 104. Between the first filter system and the percolate reservoir 20, a flow measuring device 128 is arranged which detects the throughput of percolate in the first and/or the second main drainage line 102 and 104. On the basis of the detected data and of additional data, the valves may be controlled in an optimum manner.

Figure 3:
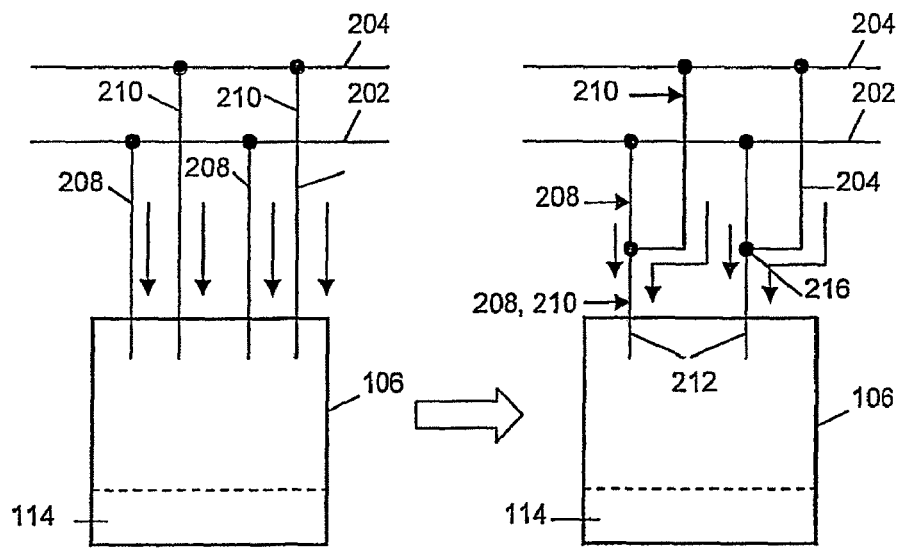
FIG. 3 is a schematic representation of a circuit detail of the percolate distributing means.

In analogy with the first and second main drainage line 102 and 104 of the percolate drainage means 100, the percolate distributing means 200 includes a first and a second main distribution line 202 and 204 (also cf. FIG. 3) which open into the first and the second percolate container 22 and 24, respectively. Each of the digestion tanks 106 is connected to the first main distribution line 202 via two first digestion tank distribution lines 208, and to the second main distribution line 204 via two second digestion tank distribution lines 210 (see FIG. 3). One of the first digestion tank distribution lines 208 and one of the second digestion tank distribution lines 210 are connected to each other so as to include a common main distributing section 212 extending from a gas region of the digestion tank 106 as far as a connection point 216, and a first and a second secondary distributing section 218 and 220 extending from the connection point 216 to the first and the second main distribution line 202 and 204, respectively. The second one of the first digestion tank distribution lines 208 and the second one of the second digestion tank distribution lines 210 are connected to each other correspondingly. In other words, the first digestion tank distribution lines 208 each include a main distributing section 212 and a secondary distributing section 218, and the second digestion tank distribution lines 210 each include a main distributing section 214 and a secondary distributing section 220.

In each secondary distributing section 218, 220 a respective flow control valve 224 is arranged, and in each main distributing section 212 a respective cut-off valve 228 is arranged. Between the digestion tanks 106 and the percolate reservoir 20, a filter system 226 is arranged in the main distribution lines 202, 204. Furthermore, pumps 230 for conveying the percolate from the percolate reservoir 20 into the respective digestion tanks 106 as well as flow control valves 232 and cut-off valves 234 are arranged inside the main distribution lines 202, 204. In analogy with the percolate drainage means 100, as a result of appropriate positions of the valves 224 and 228 it is possible to either jointly supply the percolate from the first and second percolate containers 22 and 24 or to separately supply the percolate from only one of the first and second percolate containers 22 and 24 to each one of the digestion tanks 106. In other words, the valves 224, 228 allow on arbitrary percolate mixture from the first and/or the second percolate container 22 and 24 to be supplied for each one of the digestion tank 106, independently of the other ones of the digestion tanks 106, with this mixture then being distributed over the biomass by means of the main distributing sections 212. In analogy with the percolate drainage means 100, a flow measuring device for detecting the throughput of percolate in the first and/or the second main distribution line 202 and 204 is arranged between the filter system 226 and the percolate reservoir 20.

The digestion tanks 106 each include a biogas discharge conduit (not shown) through which the biogas generated in the respective digestion tank 106 is discharged.

In accordance with the embodiment, all of the valves and pumps are driven by a percolate regulation unit (not shown). Regulation is performed, for example, on the basis of the detected values of the percolate level which may be detected, e.g., with the aid of a pressure sensor, the temperature of the biomass, the composition of the discharged biogas, etc.

Although the present invention has been disclosed with reference to the preferred embodiments so as to enable an enhanced comprehension of these, it should be understood that the invention may be realized in various ways without departing from the scope of the invention. Accordingly, the invention should be construed to the effect of encompassing any possible embodiments and aspects for the shown embodiments which may be realized without departing from the scope of the invention as set forth in the annexed claims.

The invention claimed is:

1. A biogas plant for separately methanizing two types of biomass each having a high solids fraction, said biogas plant comprising:
    a digestion tank system having a plurality of digestion tanks adapted to be closed in a gas- and liquid-tight manner, each of which includes a charging and withdrawing opening for charging with biomass and withdrawing the biomass;
    a biogas discharge means;
    a percolate reservoir;
    a percolate drainage means for discharging percolate from the plurality of digestion tanks and supplying the percolate to the percolate reservoir;
    a percolate distributing means for distributing the percolate from the percolate reservoir over the biomass in the plurality of digestion tanks; and
    a percolate regulating means for regulating the percolate level in the plurality of digestion tanks;
    wherein the percolate reservoir includes a first and a second percolate container;
    wherein supplying and discharging of the percolate to and from the first and/or the second percolate container takes place with the aid of the percolate regulating means;
    wherein the plurality of digestion tanks is divided into a first subset of digestion tanks having a first type of biomass, the first subset of digestion tanks connected to the first percolate container, and a second subset of digestion tanks having a second type of biomass, the second subset of digestion tanks connected to the second percolate container; and
    wherein the percolate from the first percolate container is discharged to the first subset of digestion tanks and the first type of biomass, and the percolate from the second percolate container is discharged to the second subset of digestion tanks and the second type of biomass.

2. The biogas plant according to claim 1, characterized in that:
    the percolate drainage means includes a first and a second main drainage line for connecting the first and the second percolate container to the digestion tanks;
    the first and the second main drainage line branch into first and second digestion tank drainage lines, wherein one of the first and one of the second digestion tank drainage lines, which open into a percolate region of the digestion tank, are associated to each one of the plurality of digestion tanks.

3. The biogas plant according to claim 2, characterized in that between the digestion tank system and the percolate reservoir, a drainage filter system is arranged in the first and/or the second main drainage line.

4. The biogas plant according to claim 2, characterized in that the first and the second digestion tank drainage line of a digestion tank are subdivided at a branching point into a first secondary drainage section connected to the first main drainage line and a second secondary drainage section connected to the second main drainage line and a common main drainage section extending into the digestion tank, and in that a cut-off valve is arranged in each one of the secondary drainage sections.

5. The biogas plant according to claim 4, characterized in that the valves are valves which are adapted to be operated pneumatically.

6. The biogas plant according to claim 2, characterized in that each digestion tank drainage line includes a pump for conveying percolate into the percolate reservoir.

7. The biogas plant according to claim 1, characterized in that each digestion tank includes a filling level sensor for determining a percolate level, which is connected to the percolate regulation unit.

8. The biogas plant according to claim 1, characterized in that:
the percolate distributing means includes a first and a second main distribution line which connect the first and the second percolate container to the digestion tanks;
the first and the second main distribution line branch into respective first and second digestion tank distribution lines, wherein one of the first and one of the second digestion tank distribution lines, which open into a gas region of the digestion tank, are associated to each one of the plurality of digestion tanks.

9. The biogas plant according to claim 8, characterized in that the first and the second digestion tank distribution line of a digestion tank are subdivided at a connection point into first and a second secondary distributing sections and a common main distributing section extending into the digestion tank, and in that a flow control valve is arranged in each one of the secondary distributing sections.

10. The biogas plant according to claim 9, characterized in that into each one of the digestion tanks there extend a plurality of main distributing sections, each of which branch at the connection point into the first secondary distributing section connected to the first main distribution line and the second secondary distributing section connected to the second main distribution line.

11. The biogas plant according to claim 8, characterized in that between the digestion tank system and the percolate reservoir, a distribution filter system is arranged in the first and/or the second main distribution line.

12. The biogas plant according to claim 8, characterized in that in each one of the main distributing sections a cut-off valve is arranged.

13. The biogas plant according to claim 1, characterized in that at least three separate percolate circuits having at least one third percolate container, at least one third main distribution line, and at least one third main drainage line are provided.

14. The biogas plant according to claim 1, characterized in that the single percolate containers are arranged in a nested configuration.

15. The biogas plant according to claim 1, characterized in that the single percolate containers are realized in the form of concentric pipes.

16. The biogas plant according to claim 1, characterized in that the charging and withdrawing opening is a flap adapted to be actuated hydraulically, which closes the digestion tank at ground level.

17. The biogas plant according to claim 1, characterized in that the plurality of digestion tanks each include a retaining means which is arranged behind the flap in the digestion tank when viewed in the direction of charging, such that charged biomass is at least partly supported against the retaining means.

* * * * *